(12) United States Patent
Yoshioka et al.

(10) Patent No.: US 10,292,876 B2
(45) Date of Patent: May 21, 2019

(54) PULL-ON DISPOSABLE DIAPER

(71) Applicant: UNICHARM CORPORATION, Shikokuchuo-shi, Ehime (JP)

(72) Inventors: Toshiyasu Yoshioka, Kanonji (JP); Jun Fukasawa, Kanonji (JP); Noriko Nagase, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 15/774,836

(22) PCT Filed: Jun. 24, 2016

(86) PCT No.: PCT/JP2016/068798
§ 371 (c)(1),
(2) Date: May 9, 2018

(87) PCT Pub. No.: WO2017/081880
PCT Pub. Date: May 18, 2017

(65) Prior Publication Data
US 2018/0325749 A1    Nov. 15, 2018

(30) Foreign Application Priority Data
Nov. 10, 2015 (JP) ................... 2015-220184

(51) Int. Cl.
*A61F 13/493* (2006.01)
*A61F 13/551* (2006.01)
(Continued)

(52) U.S. Cl.
CPC ........ *A61F 13/5512* (2013.01); *A61F 13/493* (2013.01); *A61F 13/496* (2013.01);
(Continued)

(58) Field of Classification Search
CPC ................ A61F 13/493; A61F 13/551; A61F 13/55102; A61F 13/5512; A61F 2013/1504; A61F 2013/55125
See application file for complete search history.

(56) References Cited

U.S. PATENT DOCUMENTS 5,358,500 A    10/1994  Lavon et al.
6,645,188 B2 *  11/2003  Kusibojoska ......... A61F 13/496
                                                   604/385.11
(Continued)

FOREIGN PATENT DOCUMENTS

CN    1140984 A     1/1997
CN    102245145 A   11/2011
(Continued)

OTHER PUBLICATIONS

Written Opinion in PCT/JP2016/068798, dated Sep. 13, 2016, 9 pp.
(Continued)

*Primary Examiner* — Catharine L Anderson
(74) *Attorney, Agent, or Firm* — Hauptman Ham, LLP

(57) ABSTRACT

A pull-on disposable diaper includes a front side portion; a back side portion; a crotch portion; a waist opening; and a pair of leg openings. An edge portion of the waist opening of the front side portion includes a recessed portion that is recessed in the lengthwise direction toward the crotch portion with respect to an edge portion of the waist opening of the back side portion. A tape member is fixed on a non-skin side surface of the back side portion so as to be extendable toward the waist opening in the lengthwise direction, the tape member being used for fixing the diaper in a small state in the lengthwise direction when the diaper is disposed of. The recessed portion is provided at a position corresponding to the tape member in the lateral direction.

9 Claims, 12 Drawing Sheets

(51) Int. Cl.
*A61F 13/496* (2006.01)
*A61F 13/49* (2006.01)
*A61F 13/53* (2006.01)
*A61F 13/15* (2006.01)

(52) U.S. Cl.
CPC ........ *A61F 13/49009* (2013.01); *A61F 13/53* (2013.01); *A61F 2013/1504* (2013.01); *A61F 2013/55125* (2013.01)

(56) References Cited

U.S. PATENT DOCUMENTS

| | | | | |
|---|---|---|---|---|
| 6,656,171 | B1* | 12/2003 | Matsuda | A61F 13/5512 156/204 |
| 6,926,704 | B2* | 8/2005 | Andersson | A61F 13/5512 604/385.13 |
| 7,641,641 | B2* | 1/2010 | Ramshak | A61F 13/493 604/385.01 |
| 7,867,208 | B2* | 1/2011 | Samuelsson | A61F 13/5512 604/385.11 |
| 7,947,028 | B2* | 5/2011 | Cohen | A61F 13/5633 604/385.01 |
| 7,985,210 | B2* | 7/2011 | Ashton | A61F 13/493 604/317 |
| 8,016,971 | B2 | 9/2011 | Stabelfeldt et al. | |
| 8,506,546 | B2* | 8/2013 | Buhrow | A61F 13/493 2/111 |
| 8,822,752 | B2* | 9/2014 | Fukae | A61F 13/551 604/359 |
| 9,259,366 | B2* | 2/2016 | Takino | A61F 13/622 |
| 2002/0177836 | A1 | 11/2002 | Hayase et al. | |

FOREIGN PATENT DOCUMENTS

| | | |
|---|---|---|
| CN | 103764087 A | 4/2014 |
| CN | 104095712 A | 10/2014 |
| JP | 8-10305 A | 1/1996 |
| JP | H8-510942 A | 11/1996 |
| JP | 2003-305082 A | 10/2003 |
| JP | 2005-13598 A | 1/2005 |
| JP | 2005-237768 A | 9/2005 |
| JP | 2005-287662 A | 10/2005 |
| JP | 2006-43068 A | 2/2006 |
| JP | 2006-238989 A | 9/2006 |
| JP | 2010-131111 A | 6/2010 |
| JP | 2011-136082 A | 7/2011 |
| JP | 2012-135446 A | 7/2012 |
| JP | 2012-192115 A | 10/2012 |
| JP | 2014-61255 A | 4/2014 |
| JP | 2014-121409 A | 7/2014 |
| WO | 2010/070477 A2 | 6/2010 |

OTHER PUBLICATIONS

Extended European Search Report in EP Application No. 16863844.3, dated Oct. 4, 2018, 5pp.
Office Action in JP Application No. 2015-252865, dated Jul. 3, 2018, 2pp.
Office Action in JP Application No. 2015-220183, dated Jul. 10, 2018, 3pp.
Office Action in JP Application No. 2015-131815, dated Aug. 14, 2018, 3pp.
International Search Report in PCT/JP2016/068798, dated Sep. 13, 2016, 3pp.
Office Action in CN Application No. 201680065319.X, dated Jan. 9, 2019, 5pp.

* cited by examiner

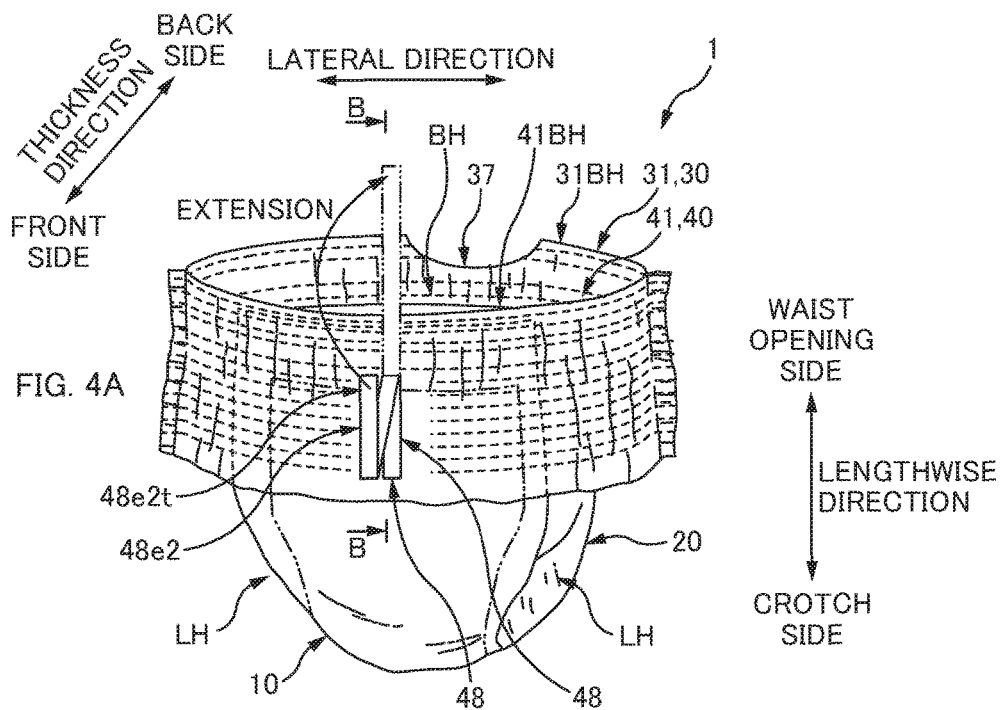
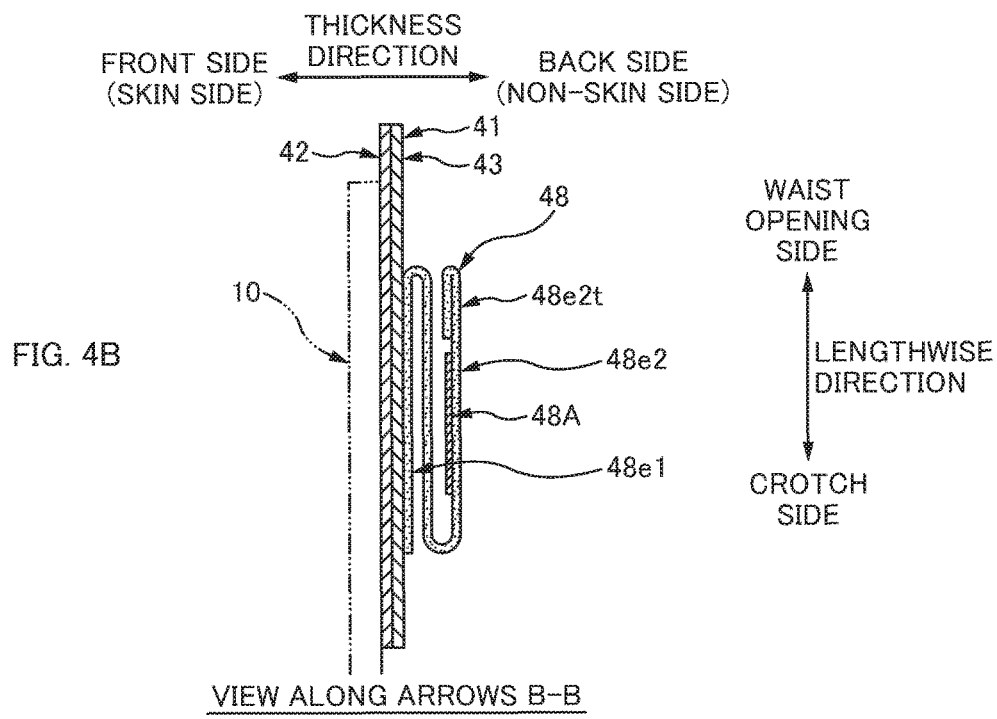

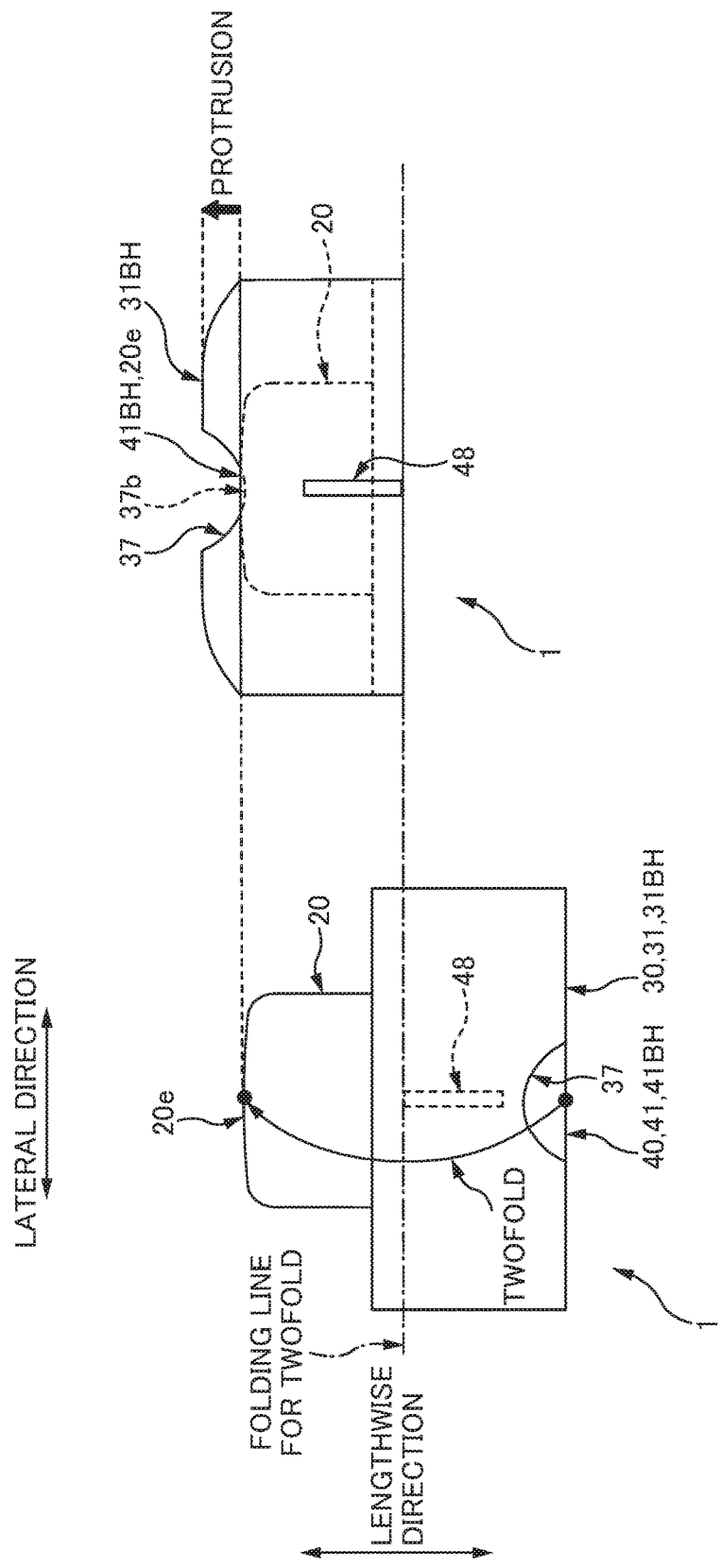

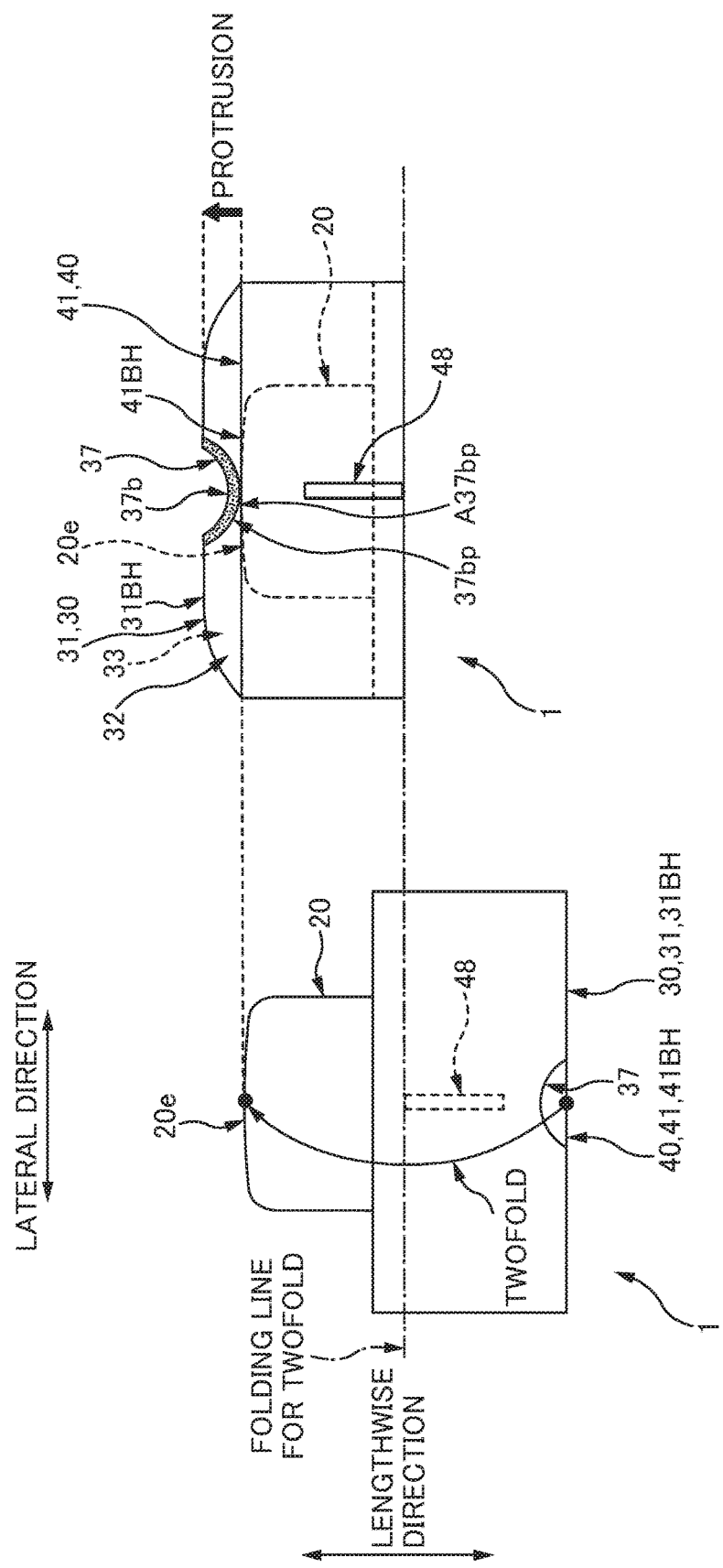

PULL-ON DISPOSABLE DIAPER

RELATED APPLICATIONS

The present application is a national phase of International Application Number PCT/JP2016/068798, filed Jun. 24, 2016, which claims priority to Japanese Application Number 2015-220184, filed Nov. 10, 2015.

TECHNICAL FIELD

The present disclosure relates to a pull-on disposable diaper.

BACKGROUND ART

Pull-on disposable diapers are conventionally used.

The pull-on disposable diapers each include a lengthwise direction and a lateral direction orthogonal to each other. Furthermore, the diapers each include a front side portion located on a front side of a wearer, a back side portion located on a back side of the wearer, and a crotch portion located at a crotch part of the wearer. The front side portion and the back side portion are continuous at respective positions of both ends in the lateral direction, thereby forming a waist opening on one side in the lengthwise direction. Moreover, the front side portion and the back side portion are continuous through the crotch portion on another side in the lengthwise direction, thereby forming a pair of leg openings on both sides in the lateral direction of the crotch portion.

FIG. 1A and FIG. 1B are explanatory views of disposal treatment that is performed after using a diaper 1'.

Firstly, as illustrated in FIG. 1A, the diaper 1' is rolled in the lengthwise direction from a crotch portion 20' side in the lengthwise direction while making a front side portion 30' inside, so that the diaper 1' is made in a compact state with a small size in the lengthwise direction as illustrated in FIG. 1B. Next, a post-treatment tape 48' provided on a non-skin side surface of a back side portion 40' is extended toward a waist opening BH', and thus the post-treatment tape 48' extends beyond edge portions 30BH', 40BH' of the waist opening BH' in the lengthwise direction. Then, an end portion 48e' of the post-treatment tape 48' in the lengthwise direction is fastened with adhesive layer or the like of the end portion 48e' at a part 1p' of the diaper, which is located beyond the edge portions 30BH', 40BH'. Accordingly, the diaper 1' is held in the above-stated compact state to be disposed of (PTL 1).

CITATION LIST

Patent Literature

[PTL 1] Japanese Examined Utility Model Publication No. H8-10305

SUMMARY OF INVENTION

Technical Problem

However, when the diaper 1' is rolled, a phenomenon similar to a so-called inner wheel difference of a vehicle (hereinafter, referred to as an inner wheel difference phenomenon) may occur. In other words, since the front side portion 30' is made inside when the diaper 1' is rolled from the crotch portion 20' side, the edge portion 30BH' of the waist opening BH' of the front side portion 30' largely protrudes in the lengthwise direction with respect to the edge portion 40BH' of the waist opening BH' of the back side portion 40'. Thus, the part 1p' of the diaper which is located so as to extend beyond these edge portions 30BH', 40BH' in the lengthwise direction becomes apart from the post-treatment tape 48' in the lengthwise direction by the extent that the former edge portion 30BH' protrudes in the lengthwise direction. As a result, it becomes difficult to securely fasten the post-treatment tape 48' to the part 1p'.

The present disclosure has been made in view of conventional problems such as that described above and an objective thereof is to firmly fasten a tape member to a part of the diaper, which is located beyond the edge portion of the waist opening, the tape member such as a post-treatment tape being used for disposal of a diaper.

Solution to Problem

A main aspect of the invention for achieving the aforementioned object is a pull-on disposable diaper including a lengthwise direction and a lateral direction orthogonal to each other, the pull-on disposable diaper including: a front side portion; a back side portion; a crotch portion; a waist opening; and a pair of leg openings, an edge portion of the waist opening of the front side portion including a recessed portion that is recessed in the lengthwise direction toward the crotch portion with respect to an edge portion of the waist opening of the back side portion, a tape member being fixed on a non-skin side surface of the back side portion so as to be extendable toward the waist opening in the lengthwise direction, the tape member being used for fixing the diaper in a small state in the lengthwise direction when the diaper is disposed of, the recessed portion being provided at a position corresponding to the tape member in the lateral direction.

Other features of the present invention will be made clear by the description and attached drawings.

Advantageous Effects of Invention

According to the present disclosure, a tape member such as a post-treatment tape used for the disposal of a diaper can be securely fastened to a part of the diaper which is located beyond an edge portion of a waist opening.

BRIEF DESCRIPTION OF DRAWINGS

FIG. 4A is a schematic perspective view when the diaper 1 in a pull-on state is seen from a back side, and FIG. 4B is a schematic enlarged view along arrows B-B in FIG. 4A.

FIG. 7A and FIG. 7B are schematic plan views when the diaper 1 is folded in two, the diaper 1 including a recessed portion 37 having a depth L37d which is deep.

FIG. 8A and FIG. 8B are schematic plan views when the diaper 1 is folded in two, the diaper 1 including a recessed portion 37 having a depth L37d which is shallow.

DESCRIPTION OF EMBODIMENTS

Figure 1A:
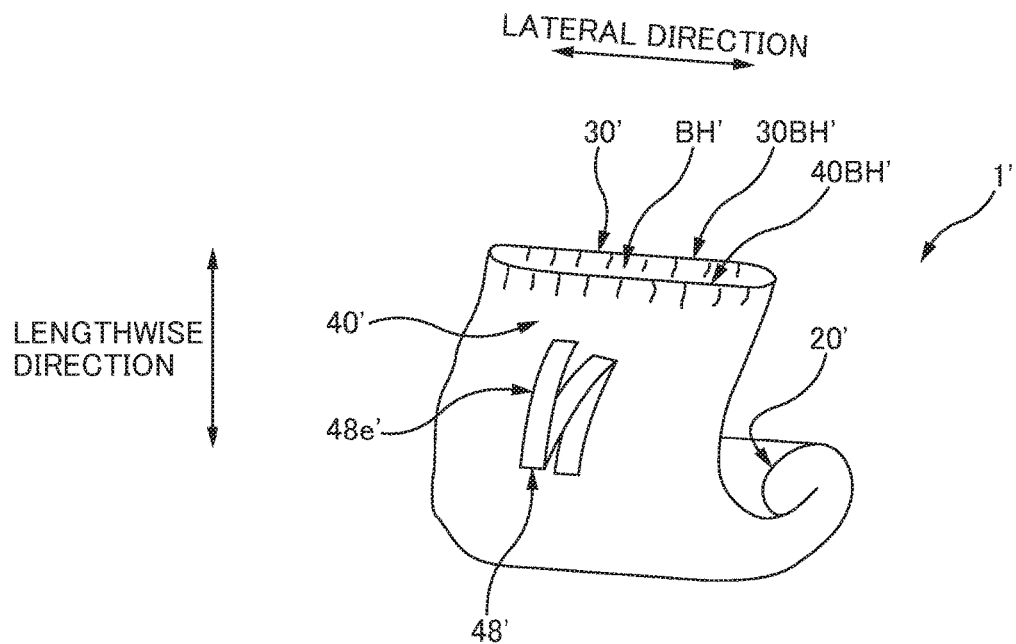
FIG. 1A and FIG. 1B are explanatory views each illustrating disposal treatment performed after using a pull-on disposable diaper 1'.
Figure 1B:
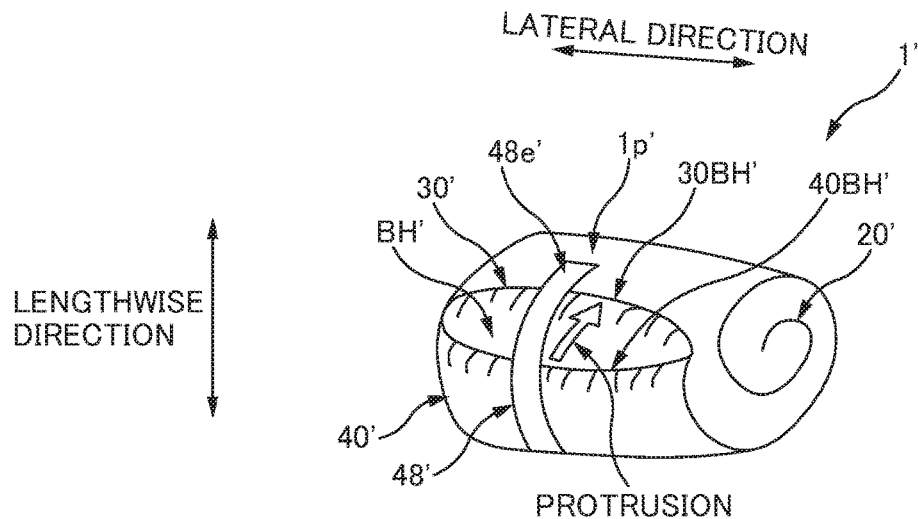

At least the following matters will be made clear by the description in the present specification and the accompanying drawings.

Disclosed a pull-on disposable diaper including a lengthwise direction and a lateral direction orthogonal to each other, the pull-on disposable diaper including: a front side portion; a back side portion; a crotch portion; a waist opening; and a pair of leg openings, an edge portion of the waist opening of the front side portion including a recessed portion that is recessed in the lengthwise direction toward the crotch portion with respect to an edge portion of the waist opening of the back side portion, a tape member being fixed on a non-skin side surface of the back side portion so as to be extendable toward the waist opening in the lengthwise direction, the tape member being used for fixing the diaper in a small state in the lengthwise direction when the diaper is disposed of, the recessed portion being provided at a position corresponding to the tape member in the lateral direction.

According to such a pull-on disposable diaper, the recessed portion that is recessed in the lengthwise direction toward the crotch portion with respect to an edge portion of the waist opening of the back side portion is formed at the edge portion of the waist opening of the front side portion, and the recessed portion is provided at a position corresponding to the tape member in the lateral direction. Thus, even if the aforementioned inner wheel difference phenomenon occurs when the diaper is made in the compact state described above for disposing of the diaper, the distance from the tape member, to a part of the diaper can be shortened by this recessed portion, the part being located beyond the edge portion of the waist opening in the lengthwise direction. Accordingly, when the tape member is extended toward the waist opening in the lengthwise direction, the tape member can easily reach, through the recessed portion, the part of the diaper which is located beyond the edge portion of the aforementioned waist opening. As a result, the tape member can be securely fastened to the above part.

In the pull-on disposable diaper, it is preferable that a center position of the tape member in the lateral direction is included in the recessed portion in the lateral direction.

According to such a pull-on disposable diaper, when the tape member is extended toward the waist opening in the lengthwise direction, more parts of the tape member can be included in the aforementioned recessed portion. Thus, the tape member can more easily reach, through the recessed portion, the part of the diaper which is located beyond the edge portion of the waist opening.

In the pull-on disposable diaper, it is preferable that a maximum value of a dimension of the recessed portion in the lateral direction is greater than a maximum value of a dimension of the tape member in the lateral direction.

According to such a pull-on disposable diaper, when the tape member is extended toward the waist opening in the lengthwise direction, the tape member can be included in the aforementioned recessed portion over the entire length of the tape member in the lateral direction.

Accordingly, the tape member can more easily reach, through the recessed portion, the part of the diaper which is located beyond the edge portion of the waist opening.

In the pull-on disposable diaper, it is preferable that in a state in which an edge portion of the waist opening of the back side portion and an end portion of the crotch portion in the lengthwise direction are overlapped at mutual center positions in the lateral direction by folding the diaper in two in the lengthwise direction so that the front side portion is positioned inside, a bottom of the recessed portion does not protrude in the lengthwise direction with respect to an edge portion of the waist opening of the back side portion.

According to such a pull-on disposable diaper, the bottom of the aforementioned recessed portion of the front side portion does not protrude in the lengthwise direction with respect to the edge portion of the waist opening of the back side portion. Accordingly, the tape member can more easily reach the part of the diaper which is located beyond the edge portion of the waist opening.

In the pull-on disposable diaper, it is preferable that in a state in which an edge portion of the waist opening of the back side portion and an end portion of the crotch portion in the lengthwise direction are overlapped at mutual center positions in the lateral direction by folding the diaper in two in the lengthwise direction so that the front side portion is positioned inside, a bottom of the recessed portion protrudes in the lengthwise direction with respect to the edge portion.

According to such a pull-on disposable diaper, the bottom of the aforementioned recessed portion of the front side portion protrudes in the lengthwise direction with respect to the edge portion of the waist opening of the back side portion. Accordingly, the tape member can be fastened not only to the edge portion of the waist opening of the back side portion, but also to the bottom of the aforementioned recessed portion of the front side portion.

In the pull-on disposable diaper, it is preferable that a bottom-containing portion including the bottom of the recessed portion in the front side portion includes a different color region that can be visually recognized from a skin side by a color different from a color of the end portion of the crotch portion.

According to such a pull-on disposable diaper, the bottom of the recessed portion is easily visually recognized in a state in which the diaper is made small in the lengthwise direction. Thus, a caretaker who disposes of the diaper can fasten the tape member to the diaper through the recessed portion without mistaking a target part to which the tape member is to be fastened in the diaper.

In the pull-on disposable diaper, it is preferable that the tape member is provided in a center portion of the back side portion in the lateral direction, and the recessed portion is formed in a center portion of the front side portion in the lateral direction.

According to such a pull-on disposable diaper, since the recessed portion is formed at the center portion of the front side portion in the lateral direction, the diaper can be placed so as not to contact with the wearer's navel. Thus, when it is not preferable to place the diaper on the wearer's navel, for example, in a case in which the navel of a newborn infant is moist or a clip for preventing bleeding is attached to the navel, this diaper is a suitable diaper.

In the pull-on disposable diaper, it is preferable that the diaper includes an absorbent core that absorbs excrement, the diaper includes elastic members that impart contractile force in the lengthwise direction and the lateral direction, and in a virtual state in which the contractile force is not imparted at all, a maximum value of a dimension of the recessed portion in the lateral direction is smaller than a maximum value of a dimension of the absorbent core in the lateral direction.

According to such a pull-on disposable diaper, the maximum value of the dimension of the recessed portion in the lateral direction is smaller than the maximum value of the dimension of the absorbent core in the lateral direction. Thus, the dimension of the recessed portion can be made to have a minimum required size for preventing the diaper from contacting with the wearer's navel. This can largely secure a portion contacting with the skin of the wearer in the waist opening of the diaper, so that this portion can provide an excellent fitting property to the skin.

In the pull-on disposable diaper, it is preferable that a number of stacked sheets in a recessed portion-containing portion that includes the recessed portion in the front side portion is greater than a number of stacked sheets in a portion positioned on both sides in the lateral direction of the recessed portion-containing portion in the front side portion.

According to such a pull-on disposable diaper, the stiffness of the recessed portion-containing portion in the front side portion is high, thereby preventing the recessed portion from being deformed. As a result, the tape member can more easily reach, through the recessed portion, the part of the diaper which is located beyond the edge portion of the waist opening.

In addition, since the stiffness of the portions positioned on both sides in the lateral direction of the recessed portion-containing portion in the front side portion is low, the portions can be easily deformed. Thus, the diaper can be made compact at the time of disposal, so that the diaper is easily disposed of.

Present Embodiment

Figure 2:
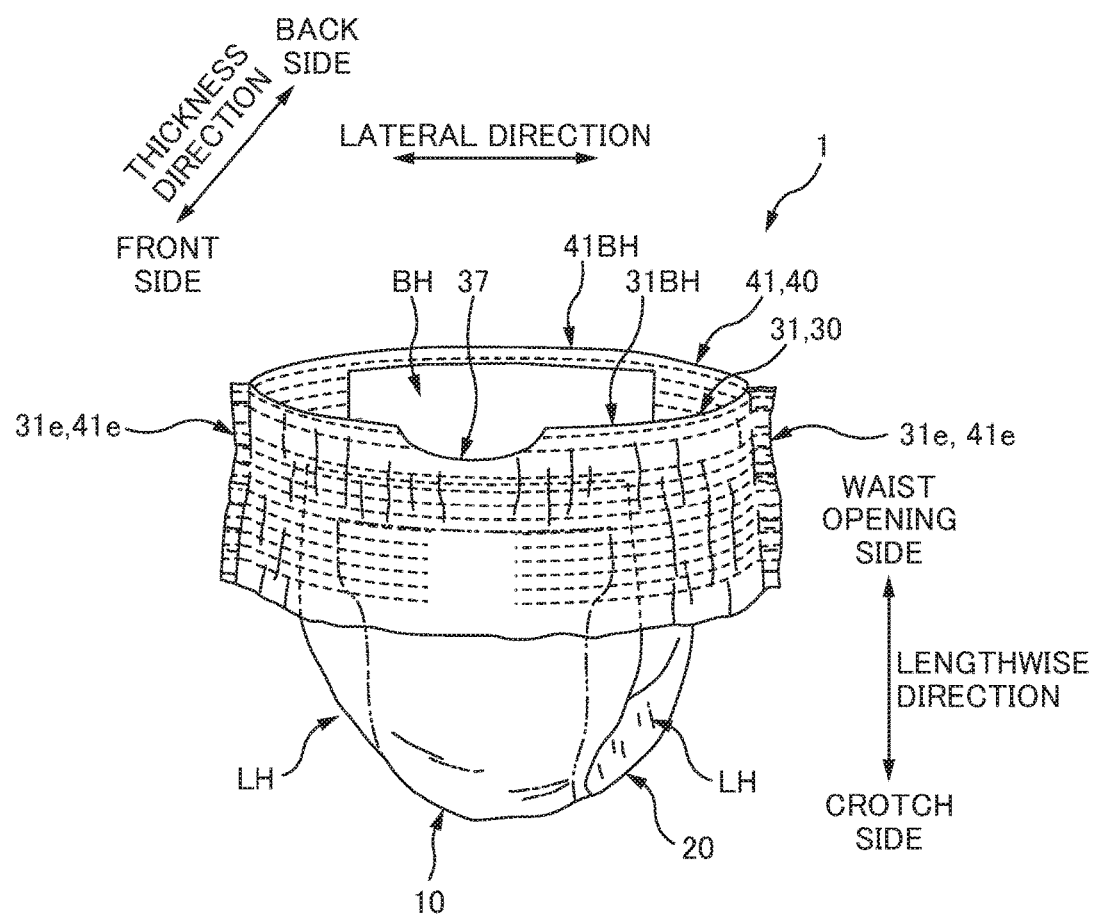
FIG. 2 is a schematic perspective view of a three-piece type diaper 1 when seen from a front side as an example of the pull-on disposable diaper 1 of the present embodiment.
Figure 3A:
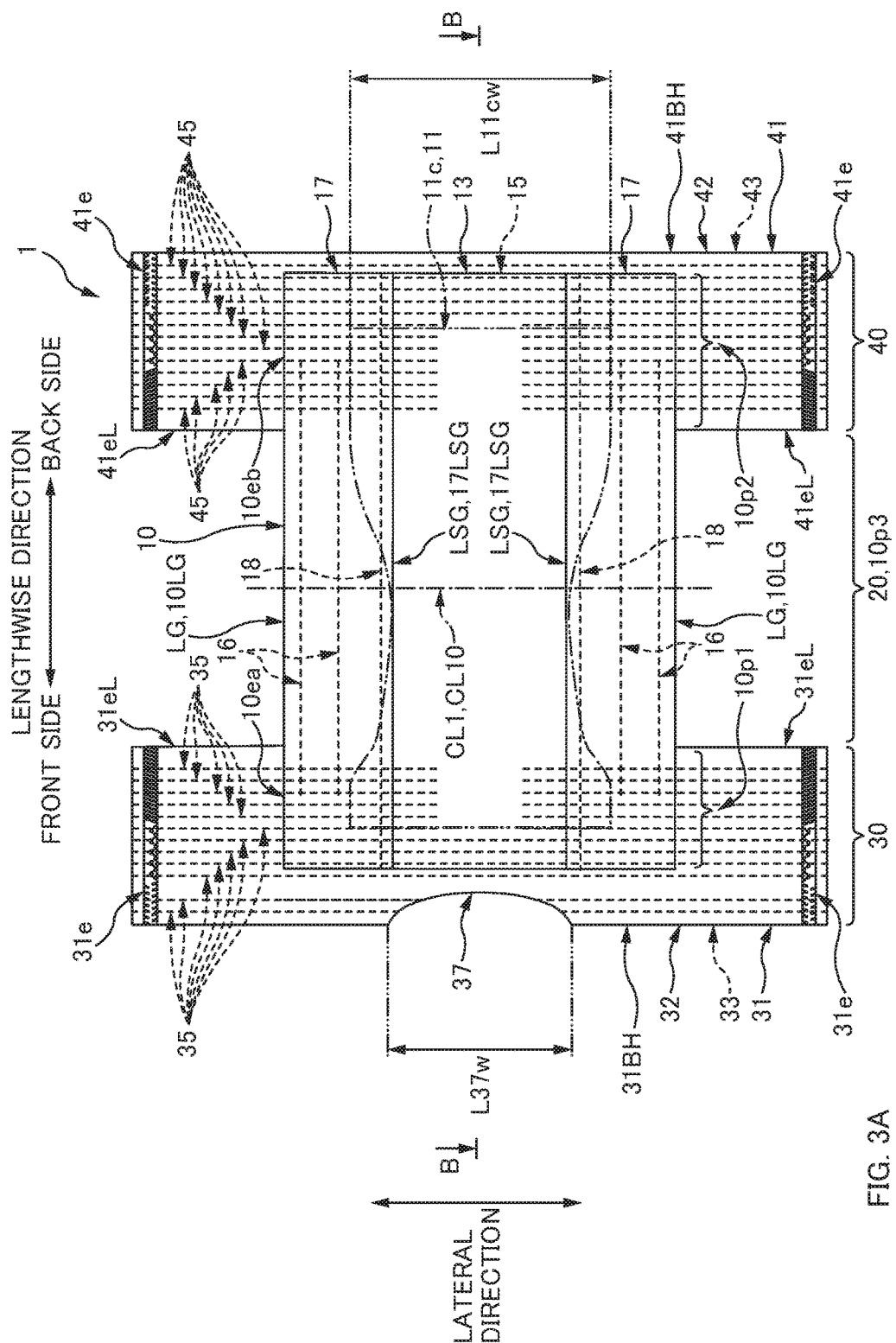
FIG. 3A is a schematic plan view when the diaper 1 in a developed-state is seen from a skin side.
Figure 3B:
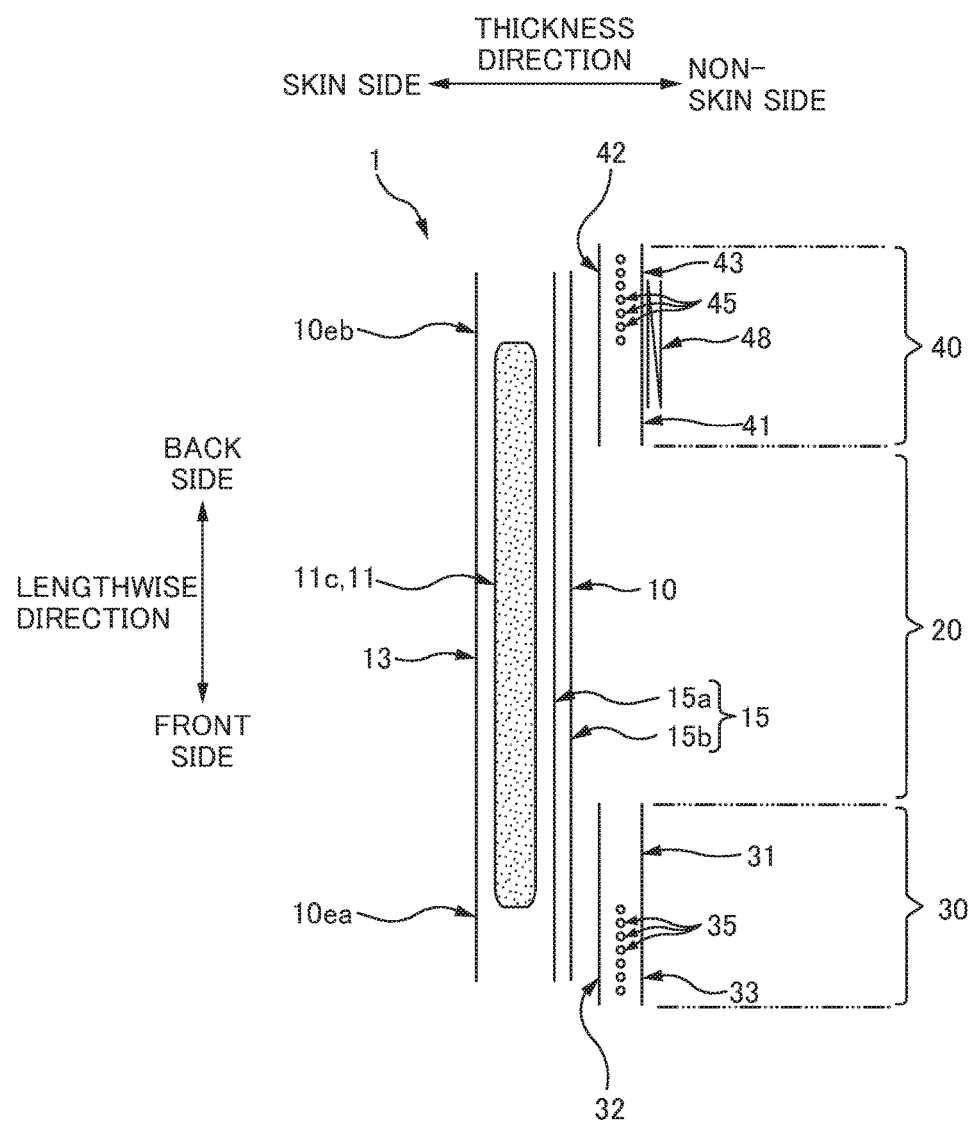
FIG. 3B is a cross-sectional view taken along line B-B of FIG. 3A.

FIG. 2 is a schematic perspective view when a three-piece type diaper 1, which is an example of a pull-on disposable diaper 1 of the present embodiment, is seen from a front side. FIG. 3A is a schematic plan view when the diaper 1 in a developed state is seen from a skin side, and FIG. 3B is a cross-sectional view taken along line B-B of FIG. 3A. Moreover, FIG. 4A is a schematic perspective view when the diaper 1 is seen from a back side, and FIG. 4B is a schematic enlarged view along arrows B-B in FIG. 4A.

The diaper 1 includes a lengthwise direction, a lateral direction and a thickness direction as three directions orthogonal to one another in a pull-on state of FIG. 2. In the following, one side and another side in the lengthwise direction in the pull-on state are also referred to as "a waist opening side" and "a crotch side", respectively, and one side and another side in the thickness direction are also referred to as "a front side" and "a back side", respectively.

Also in the developed states in FIG. 3A and FIG. 3B, the diaper 1 includes a lengthwise direction, a lateral direction and a thickness direction as three directions orthogonal to one another. In the following, one side and another side in the lengthwise direction in the developed state are also referred to as "a front side" and "a back side" respectively, and one side and another side in the thickness direction are also referred to as "a skin side" and "a non-skin side", respectively.

Note that the lateral direction in the pull-on state is synonymous with the lateral direction in the developed state. On the contrary, the lengthwise direction in the developed state is along the lengthwise direction in the pull-on state and the thickness direction in the developed state is along the thickness direction in the pull-on state.

The diaper 1 is a so-called three-piece type, thus including an absorbent main body 10 that absorbs excrement as a first component, a front-side band member 31 as a second component, and a back-side band member 41 as a third component in the developed state of FIG. 3A. Specifically, the front-side band member 31 and the back-side band member 41 are arranged in parallel with a space therebetween in the lengthwise direction, and the absorbent main body 10 is extended across both these members 31 and 41. End portions 10ea, 10eb of the absorbent main body 10 in the lengthwise direction are joined and fixed to the nearest band members 31, 41, respectively, so that the external appearance thereof is in a substantially H shape when seen in a planar view.

Then, from this developed state having the substantially H shape, the absorbent main body 10 is folded in two with a predetermined position CL10 (a position corresponding to a center position CL1 of the diaper 1 in the lengthwise direction) of the absorbent main body 10 in the lengthwise direction as a folding position. In this two-folded state, the band members 31, 41 facing each other are joined at end portions 31e, 41e in the lateral direction, respectively, by welding or the like, and then these band members 31, 41 are annularly connected, thereby forming diaper 1 in the pull-on state in which a waist opening BH and a pair of leg openings LH, LH are formed as illustrated in FIG. 2.

In the pull-on state (FIG. 2), the diaper 1 can be regarded as three divided portions 20, 30 and 40, which are different units from those described above. In other words, the diaper 1 can be divided into three portions, which are a front side portion 30 located on a front side of a wearer in the thickness direction, a back side portion 40 located on a back side of the wearer and a crotch portion 20 located at a crotch of the wearer. In this example, as illustrated in FIG. 3A, the former front side portion 30 includes a front-side band member 31 and a portion 10p1 of the absorbent main body 10, which overlaps with a front-side band member 31, the crotch portion 20 includes a portion 10p3 of the absorbent main body 10, which protrudes from the front-side band member 31 and the back-side band member 41 in the lengthwise direction, and the back side portion 40 includes the back-side band member 41 and a portion 10p2 of the absorbent main body 10, which overlaps with the back-side band member 41.

In the following, a state is referred to as a "paper pattern state", in which the diaper 1 is spread in an imaginary manner such that there is no contractile force due to the after-mentioned elastic members 16, 18, 35, 45 which are used for imparting elasticity in the lateral direction and the lengthwise direction to the diaper 1. In addition, a state in which external force in the lateral direction and the lengthwise direction does not act on the diaper 1, that is, a state in which the diaper 1 contracts in lateral direction and the lengthwise direction due to the contractile force of the above-mentioned elastic members 16, 18, 35, 45 is referred to as a "natural state". In FIG. 3A and FIG. 3B, the diaper 1 in the developed state is illustrated in a paper pattern state.

In the developed state in FIG. 3A and FIG. 3B, the absorbent main body 10 is in a substantially rectangular shape when seen in a planar view. The absorbent main body 10 is disposed so that the longitudinal direction of the absorbent main body 10 is along the lengthwise direction. The absorbent main body 10 also includes an absorbent body 11, a top sheet 13 provided to cover the absorbent body 11 from the skin side, and a back sheet 15 provided to cover the absorbent body 11 from the non-skin side.

The absorbent body 11 includes: a liquid-absorbent, absorbent core 11*c*; and a core-wrapping sheet (not shown) for wrapping the outer peripheral surface of the core 11*c*. The absorbent core 11*c* is composed of a predetermined liquid-absorbent material formed in a substantially hourglass shape when seen in a planar view, which is as an example of a predetermined shape. The liquid-absorbent material is exemplified by liquid-absorbent fiber such as pulp fiber, and by liquid-absorbent particles such as superabsorbent polymer (so-called SAP). As the core-wrapping sheet, a liquid-permeable sheet such as tissue paper or nonwoven fabric can be employed. Also, the core-wrapping sheet may be omitted. Further, the shape of the absorbent core 11*c* is not limited to the foregoing substantially hourglass shape when seen in a planar view, and may be other shape.

The top sheet 13 is a liquid-permeable sheet such as nonwoven fabric having a planar size so as to protrude from the absorbent body 11 in the lengthwise direction and the lateral direction. The back sheet 15 is also a sheet having a planar size so as to protrude from the absorbent body 11 in the lengthwise direction and the lateral direction. As an example thereof, there can be given a laminated sheet 15 having a two-layer structure (FIG. 3B). The laminated sheet 15 includes: a liquid-impermeable leak-proof sheet 15*a* such as a polyethylene film and a polypropylene film; and an exterior sheet 15*b* made of nonwoven fabric attached onto the non-skin side of the leak-proof sheet 15*a*. Both sheets 13 and 15 are joined to each other, for example, in a frame manner by bonding and welding at a portion protruding outside from the absorbent body 11 in the lengthwise direction and the lateral direction, with the absorbent body 11 being sandwiched between the top sheet 13 and the back sheet 15, thereby forming the absorbent main body 10. The back sheet 15 may not include the exterior sheet 15*b*, and may include only the leak-proof sheet 15*a*.

In addition, as in this example, leg gathers LG that respectively stretch and contract in the lengthwise direction may be provided in portions 10LG that are outside of the absorbent body 11 of the absorbent main body 10 in the lateral direction. Those leg gathers LG constitute a part of the leg openings LH. Moreover, elasticity of the leg gathers LG can be imparted by fixing elastic members 16 such as elastic strings to the aforementioned portions 10LG along the lengthwise direction in a state of being stretched in the lengthwise direction. In other words, contractile force is imparted from the elastic members 16 to the aforementioned portions 10LG in the lengthwise direction. Accordingly, each portion 10LG contracts in the lengthwise direction while forming a plurality of folds in a natural state on which the external force does not act. Thus, elasticity with which such folds fully extend is imparted to the leg gathers LG.

As in this example, a pair of leg side gathers LSG, LSG may be provided at an inner position of the leg gathers LG in the lateral direction. The leg side gathers LSG are also referred to as barrier cuffs and stand from the skin side surface of the top sheet 13 to prevent leakage of excrement in the lateral direction. In other words, leg side gather sheets 17 made of nonwoven fabric are overlapped on the skin side surface of the top sheet 13, and parts (not shown) of the sheets 17 are fixed to the top sheet 13, thereby allowing portions 17LSG positioned inner side of the parts in the lateral direction in the sheets 17 to stand. Note that the standing of the inner portions 17LSG can be achieved by fixing elastic members 18 such as elastic strings to the inner portions 17LSG along the lengthwise direction while stretching in the lengthwise direction. In other words, contractile force in the lengthwise direction is imparted to the inner portions 17LSG from the aforementioned elastic members 18, and thus the inner portions 17LSG contract in the lengthwise direction while forming a plurality of folds. Consequently, the inner portions 17LSG stand from the skin side surface of the top sheet 13.

As illustrated in FIG. 3A, the front-side band member 31 is a sheet member having a substantially rectangular shape when seen in a planar view and made of a soft sheet such as nonwoven fabric. In this example, as illustrated in FIG. 3B, the nonwoven fabrics 32, 33 are double-stacked and joined to form the front-side band member 31. As illustrated in FIG. 3A and FIG. 3B, a center portion of the front-side band member 31 in the lateral direction is overlapped and joined, from the non-skin side, with an end portion 10*ea* of the absorbent main body 10 on the front side in the lengthwise direction. In such a front-side band member 31, end portions 31*e*L (FIG. 3A) in the lengthwise direction in portions protruding from the absorbent main body 10 along the lateral direction constitute a part of the leg openings LH.

As illustrated in FIG. 3A and FIG. 3B, a plurality of elastic member 35, 35 . . . such as elastic strings along the lateral direction is arranged in the lengthwise direction while being interposed between two nonwoven fabric 32, 33 associated with the front-side band member 31, and is joined and fixed to the nonwoven fabric 32, 33 while stretching in the lateral direction. Accordingly, contractile force is imparted to the front-side band member 31 in the lateral direction. That is, elasticity is imparted to the front-side band member 31 in the lateral direction. In this example, as illustrated in FIG. 3A, the elastic members 35 are noncontinuous in a portion (for example, a center portion in the lateral direction) overlapping with the absorbent body 11 in the front-side band member 31 in order to prevent occurrence of creases of the absorbent body 11. Thus, elasticity is not imparted the above-mentioned portion. However, the invention is not limited thereto. In this example, the elastic members 35 having the same position in the lengthwise direction as a recessed portion 37 described later are also non-continuous at the position of the recessed portion 37.

As illustrated in FIG. 3A, the back-side band member 41 is a sheet member having a substantially rectangular shape when seen in a planar view and made of a soft sheet such as nonwoven fabric. In this example, as illustrated in FIG. 3B, the back-side band member 41 is formed by joining the nonwoven fabric 42, 43 in a two-layer structure. As illustrated in FIG. 3A and FIG. 3B, the center portion of the back-side band member 41 in the lateral direction is overlapped and joined, from the non-skin side, with an end portion 10eb of the absorbent main body 10 on the back side in the lengthwise direction. In such a back-side band member 41, end portions 41eL (FIG. 3A) in the lengthwise direction in portions protruding from the absorbent main body 10 along the lateral direction constitute a part of the leg openings LH.

As illustrated in FIG. 3A and FIG. 3B, a plurality of elastic members 45, 45 . . . such as elastic strings along the lateral direction is arranged in the lengthwise direction while being interposed between two nonwoven fabric 42, 43 associated with the back-side band member 41, and is joined and fixed to the nonwoven fabric 42, 43 while stretching in the lateral direction. Accordingly, contractile force is imparted to the back-side band member 41 in the lateral direction. That is, elasticity is imparted to the back-side band member 41 in the lateral direction. In this example, as illustrated in FIG. 3A, the elastic members 45 are non-continuous in a portion (for example, a center portion in the lateral direction) overlapping with the absorbent body 11 in the back-side band member 41 in order to prevent occurrence of creases of the absorbent body 11. Thus, elasticity is not imparted to the above-mentioned portion. However, the invention is not limited thereto.

Figure 5A:
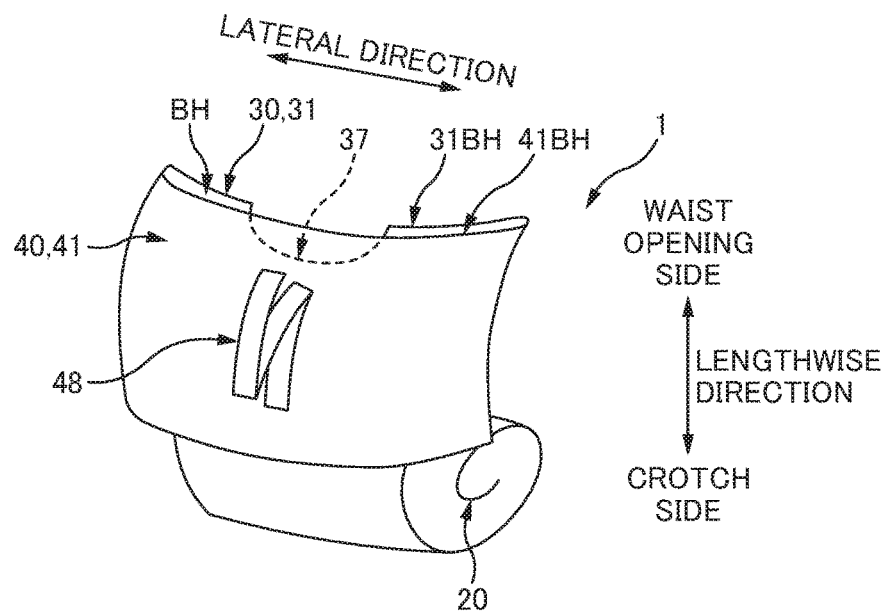
FIG. 5A and FIG. 5B are schematic perspective views each illustrating how the diaper 1 is rolled from a crotch portion 20 side in the lengthwise direction for the disposal treatment of the diaper 1 of the present embodiment.
Figure 5B:
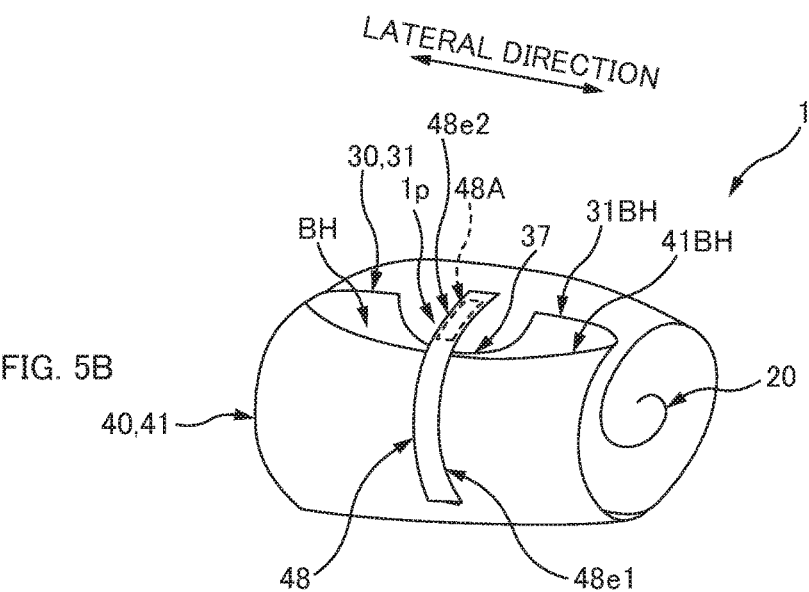

Meanwhile, as illustrated in FIG. 4A, a post-treatment tape 48 (corresponding to a tape member) is provided on the non-skin side surface of the back-side band member 41. The post-treatment tape 48 is used for disposal of the diaper 1 after use. In other words, at the time of disposal, the diaper 1 is rolled along the lengthwise direction from the crotch portion 20 in the lengthwise direction so that the front side portion 30 of the diaper 1 is positioned inside as illustrated in FIG. 5A, thereby allowing the diaper 1 to be in a compact state with a small size in the lengthwise direction as illustrated in FIG. 5B. The post-treatment tape 48 is used to fix the diaper 1 in this compact state.

As illustrated in FIG. 4A, the post-treatment tape 48 includes a band-shaped member that is long along the lengthwise direction as a main body. In a state in which the longitudinal direction and the width direction of the post-treatment tape 48 are along the lengthwise direction and the lateral direction of the diaper 1, respectively, one end portion 48e1 of the post-treatment tape 48 in the longitudinal direction is undetachably joined to the non-skin side surface of the back-side band member 41 with an adhesive (not shown) or the like. In addition, another end portion 48e2 of the post-treatment tape 48 can be extended toward the waist opening BH of the diaper 1 which is in the compact state as illustrated in FIG. 5B. Accordingly, as illustrated in FIG. 5B, an adhesive layer 48A of the other end portion 48e2 of the tape 48 is fastened to the part 1p of the diaper, which is located beyond the waist opening BH in the compact state, thus enabling the diaper 1 to be fixed in the compact state.

Note that, as illustrated in FIG. 4A and FIG. 4B, an unused post-treatment tape 48 is, for example, made into a state of being folded in a Z shape in the longitudinal direction. In other words, in the post-treatment tape 48 folded in the Z shape, at least portions of surfaces facing each other are provided with adhesive layers (not shown) having a strippable adhesive strength, thereby temporarily fixing the post-treatment tape 48 in a Z-shaped folded state. Then, a tab portion 48e2t (FIG. 4B) formed by folding a tip portion of the other end portion 48e2 is pulled in the longitudinal direction (lengthwise direction) as illustrated by double-dotted chained lines of FIG. 4A, thereby releasing the adhesion between the surfaces due to the above-mentioned adhesive layer. This can promptly extend the tape 48 toward the waist opening BH in the lengthwise direction as illustrated in FIG. 5B.

A resin material such as polyethylene or polypropylene can be exemplified as a material of the tape 48. However, the material of the tape 48 is not limited thereto. For example, the material may be a pulp material such as paper. Further, the form of the tape 48 is not limited to a form having smooth surfaces on both surfaces as stated above. For example, the form of the tape 48 may be a fiber aggregate such as nonwoven fabric or woven fabric. Moreover, a hook member of a hook-and-loop fastener may be provided instead of the adhesive layer 48A of the other end portion 48e2.

Also, in this example, the tape 48 itself is substantially non-elastic in the longitudinal direction. However, the invention is not limited thereto. That is, the tape 48 may have elasticity in the longitudinal direction by forming the tape 48 itself by an elastic material such as rubber. When the tape 48 has elasticity, the tape 48 itself contracts in the longitudinal direction, and thus the tape 48 can be in a compact state with a short length in the longitudinal direction when not used. In this case, the tape 48 may not be folded in a Z shape as shown in the aforementioned example. Note that, the folding form is not also limited to the aforementioned Z shape. For example, the folding form may be a V shape folded in two, or a W shape folded in four, or the tape 48 may be folded with more folds than the W-shaped folds.

As stated above, main components 10, 31 and 41 of the diaper 1 have been described. In the present embodiment, contrivance is made so that the problems due to the aforementioned inner wheel difference phenomenon can be solved when the diaper 1 is disposed of. That is, in the diaper 1 being in the compact state of FIG. 5B, contrivance is made so that the post-treatment tape 48 can be securely fastened to the part 1p of the diaper which is located beyond the edge portions 31BH, 41BH of the waist opening BH. In the following, this contrivance will be described.

Figure 6:
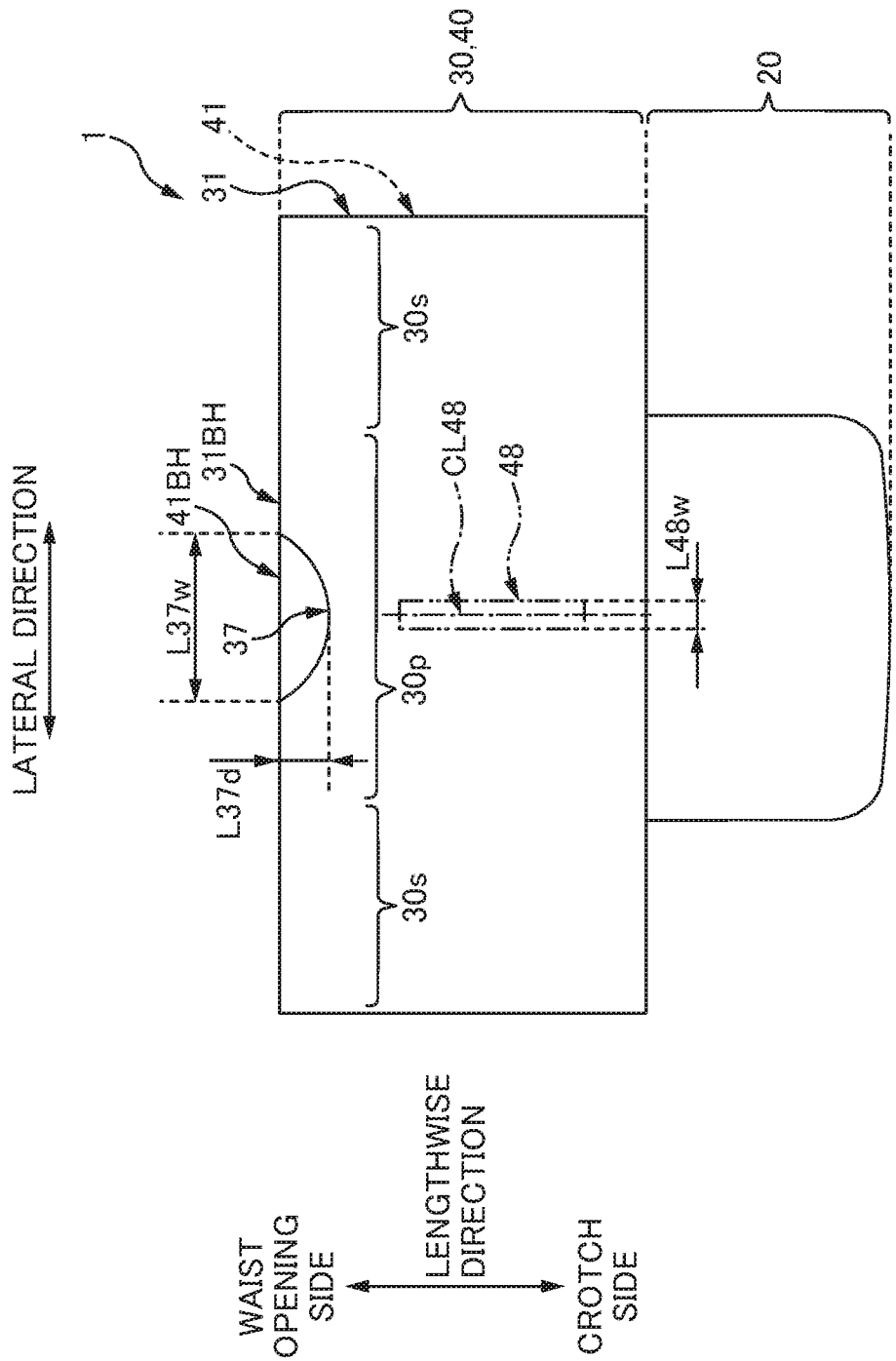
FIG. 6 is a schematic plan view of the diaper 1 in the pull-on state when it is seen from the front side.

FIG. 6 is a schematic plan view when the diaper 1 in the pull-on state of the present embodiment is seen from the front side.

In the present embodiment, firstly in the diaper 1 that is in the pull-on state and the natural state (or in a paper pattern state), an edge portion 31BH of the waist opening BH of the front-side band member 31 that belongs to the front side portion 30 includes a recessed portion 37 that is recessed in the lengthwise direction toward the crotch portion 20 with respect to an edge portion 41BH of the waist opening BH of the back-side band member 41 that belongs to the back side portion 40. In other words, although the latter edge portion 41BH is along the lateral direction and the former edge portion 31BH is also basically along the lateral direction, the former edge portion 31BH includes the recessed portion 37 at a predetermined position in the lateral direction. Note that, the presence or absence of the recessed portion 37 can be confirmed by seeing the diaper 1, in which the front side portion 30 and the back side portion 40 are overlapped in the thickness direction, from the front side in the thickness direction in a state of setting the diaper 1 on a flat surface such as a desk and making the diaper 1 flattened. In the example of FIG. 6, the recessed portion 37 has an arcuately curved shape in the paper pattern state. In this paper pattern state, a maximum value L37d of a dimension of the recessed portion 37 in the lengthwise direction is selected, for example, from the range of 10 mm to 30 mm, and is 15 mm in this example. A maximum value L37w of a dimension of the recessed portion 37 in the lateral direction is selected, for example, from the range of 50 mm to 100 mm, and is 85 mm in this example.

Furthermore, in the FIG. 6, the post-treatment tape 48 is virtually illustrated by two-dot chain lines, and the recessed portion 37 is located at a position corresponding to the post-treatment tape 48 in the lateral direction. For example, the recessed portion 37 is provided at a position in the lateral direction so as to correspond to a portion to which the post-treatment tape 48 is fixed on the non-skin side surface of the back-side band member 41 belonging to the back side portion 40. Accordingly, the recessed portion 37 overlaps with the post-treatment tape 48 in the lateral direction.

Thus, when the diaper 1 is rolled to be a compact state as illustrated in FIG. 5B, even if the aforementioned inner wheel difference phenomenon occurs, the distance from the post-treatment tape 48 to the part 1p of the diaper can be shortened by this recessed portion 37, the part 1p being located beyond the aforementioned edge portions 31BH, 41BH in the lengthwise direction. In other words, when the post-treatment tape 48 is extended toward the waist opening BH in the lengthwise direction, at least a part of the post-treatment tape 48 is allowed to be included in the aforementioned recessed portion 37, and thus the post-treatment tape 48 can reach, through the recessed portion 37, the part 1p of the diaper which is located beyond the aforementioned edge portions 31BH, 41BH. As a result, the post-treatment tape 48 can be securely fastened to the part 1p of the diaper.

In this example as illustrated in FIG. 6, a center position CL48 of the post-treatment tape 48 in the lateral direction is included in the recessed portion 37 in the lateral direction in the natural state (or the paper pattern state).

Thus, when the post-treatment tape 48 is extended toward the waist opening BH in the lengthwise direction, more parts of the post-treatment tape 48 can be included in the aforementioned recessed portion 37. Consequently, the post-treatment tape 48 can more easily reach, through the recessed portion 37, the part 1p of the diaper which is located beyond the edge portions 31BH, 41BH of the waist opening BH.

However, the invention is not limited thereto. In other words, the center position CL48 of the post-treatment tape 48 may not be included in the recessed portion 37 in the lateral direction.

Moreover, in this example as illustrated in FIG. 6, the maximum value L37w of the dimension of the recessed portion 37 in the lateral direction is larger than a maximum value L48w of the dimension of the post-treatment tape 48 in the lateral direction in the natural state (or the paper pattern state).

Thus, when the post-treatment tape 48 is extended toward the waist opening BH in the lengthwise direction, the post-treatment tape 48 can be included in the aforementioned recessed portion 37 over the entire length of the post-treatment tape 48 in the lateral direction. Accordingly, the post-treatment tape 48 can more easily reach the part 1p of the diaper which is located beyond the edge portions 31BH, 41BH of the waist opening BH, through the recessed portion 37.

However, the invention is not limited thereto. In other words, the maximum value L48w of the dimension of the post-treatment tape 48 in the lateral direction may be larger than the maximum value L37w of the dimension of the recessed portion 37 in the lateral direction.

In addition, in this example as illustrated in FIG. 6, the aforementioned recessed portion 37 is provided at a center portion of the aforementioned edge portion 31BH of the front-side band member 31 in the lateral direction in response to the fact that the post-treatment tape 48 is fixed at a center portion of the back-side band member 41 in the lateral direction.

Accordingly, the diaper 1 can be set so as not to contact with the wearer's navel. Accordingly, in a case in which it is undesirable to set the diaper 1 so as to contact with the wearer's navel, for example, in a case in which the navel of a newborn infant is moist or a clip for preventing bleeding is attached to the navel, the diaper 1 can be preferably used.

Moreover, in the developed state of FIG. 3A, the absorbent core 11c is substantially hourglass-shaped as stated above. That is, when the dimensions in the lateral direction are compared between both end portions and the center portion of the core 11c in the lengthwise direction, the former dimension in the lateral direction is larger. Accordingly, the dimension in the lateral direction is a maximum value L11cw in the both end portions, and here, the maximum value L37w of the dimension of the recessed portion 37 in the lateral direction is smaller than the maximum value L11cw of the dimension of the absorbent core 11c in the lateral direction in the aforementioned paper pattern state.

Thus, the dimension of the recessed portion 37 in the lateral direction can be made to have a minimum required size for preventing the diaper 1 from contacting with the wearer's navel. This can largely secure a portion contacting with the skin of the wearer in the waist opening BH of the diaper 1, so that this portion can provide an excellent fitting property to the skin.

As illustrated FIG. 7A and FIG. 7B, when the edge portion 41BH of the waist opening BH of the back side portion 40 and the end portion 20e of the crotch portion 20 in the lengthwise direction are overlapped at mutual center positions in the lateral direction by folding the diaper 1 in the pull-on state in two in the lengthwise direction with the front side portion 30 inside, the edge portion 31BH of the waist opening BH of the front side portion 30 protrudes in the lengthwise direction from the edge portion 41BH of the waist opening BH of the back side portion 40 as a whole based on the inner wheel difference phenomenon. Even in that case, the bottom 37b of the recessed portion 37 is allowed not to protrude from the edge portion 41BH of the waist opening BH of the back side portion 40 in the lengthwise direction in this example. In other words, the depth L37d of the recessed portion 37 in the lengthwise direction (FIG. 6) is set to such a depth that the recessed portion 37 does not protrude from the edge portion 41BH of the waist opening BH of the back side portion 40 in the lengthwise direction.

Thus, when the diaper 1 is rolled or the like to be made small and compact in the lengthwise direction, the post-treatment tape 48 can more easily reach the part 1P of the diaper, which is located beyond the edge portions 31BH, 41BH of the waist opening BH.

However, the invention is not limited thereto, and the opposite constitution may also be applicable in some cases. That is, the depth L37d of the recessed portion 37 in the lengthwise direction may be set so that the bottom 37b of the recessed portion 37 protrudes in the lengthwise direction from the edge portion 41BH of the waist opening BH of the back side portion 40 as illustrated in FIG. 8B.

In that case, the post-treatment tape 48 can be fastened not only to the edge portion 41BH of the back side portion 40 but also to the bottom 37b of the aforementioned recessed portion 37 of the front side portion 30. Accordingly, not only the edge portion 41BH of the back side portion 40 but also the edge portion 31BH of the front side portion 30 can be directly fixed by the post-treatment tape 48.

In that case, as illustrated in FIG. 8B, it is desirable that a bottom-containing portion 37bp including the aforementioned bottom 37b of the recessed portion 37 in the front-side band member 31 may include a different color region A37bp (see a dot pattern area in FIG. 8B) which can be visually recognized from the skin side by a color different from the color of the end portion 20e of the crotch portion 20. For example, in the example of FIG. 8B, the bottom-containing portion 37bp includes a region A37bp colored from the skin side in a predetermined color having a predetermined width in the lengthwise direction, and thus the region A37bp is a different color region A37bp that can be visually recognized by a color different from the color of the end portion 20e of the aforementioned crotch portion 20.

Accordingly, when the caretaker who changes the diaper makes the diaper 1 small and compact in the lengthwise direction for the disposal of the diaper 1, for example, by folding the diaper 1 in two as described above, the caretaker sees the bottom-containing portion 37bp with the end portion 20e of the aforementioned crotch portion 20 as a background picture, the end portion 20e having a color different from that of the colored region A37bp of the bottom-containing portion 37bp. This allows the bottom 37b of the recessed portion 37 to be easily visually recognized. As a result, the caretaker can fasten the post-treatment tape 48 to a fastening target portion for the post-treatment tape 48 in the diaper 1 through the recessed portion 37.

Note that, in the example of FIG. 8B, the bottom-containing portion 37bp is colored from the skin side. However, the invention is not limited thereto as long as the colored region A37bp of the bottom-containing portion 37bp can be visually recognized from the skin side. For example, since the front-side band member 31 of the front side portion 30 of the present embodiment is formed of the nonwoven fabric 32, 33, an object existing on the non-skin side can be visually recognized even from the skin side by seeing through the front-side band member 31. Thus, the bottom-containing portion 37bp may be colored from the non-skin side. Moreover, instead of coloring the two nonwoven fabric 32, 33 constituting the front-side band member 31, another sheet (not shown) may be provided so as to be overlapped with the bottom-containing portion 37bp to form the aforementioned different color region A37bp in the bottom-containing portion 37bp. In that case, the other sheet may be disposed on the skin side or the non-skin side of the front-side band member 31, or may be interposed between the two nonwoven fabric 32, 33 of the front-side band member 31.

Note that the "different color" stated here refers to two colors in which the color difference between the two regions for comparison can be perceived with the unaided eye. The "color difference" can be obtained by using a commercially available colorimeter to perform colorimetry on two points (two regions) for measurement, and then comparing numerical values obtained based on the CIE1976 (L*a*b*) color space defined in JIS Z 8729 or the like. Specifically, letting $\Delta L^*$ be the difference between the L* values of the two points for measurement, $\Delta a^*$ be the difference between the a* values, and $\Delta b^*$ be the difference between the b* values, the color difference can be obtained by the following equation, $\Delta E^*ab=[(\Delta L^*)^2+(\Delta a^*)^2+(\Delta b^*)^2]^{1/2}$. Here, it is assumed that "have mutually different colors" is satisfied if this color difference $\Delta E^*ab$ is greater than or equal to 1.5, or desirably greater than or equal to 3.0. If the value of $\Delta E^*ab$ is greater than or equal to 1.5, it can be said that the colors are different to the extent of being detectable by a human with the unaided eye, and thus the caretaker who changes the diaper can recognize the different color region A37bp associated with the bottom 37b of the recessed portion 37 with the end portion 20e of the crotch portion 20 used as a background picture.

Figure 9A:
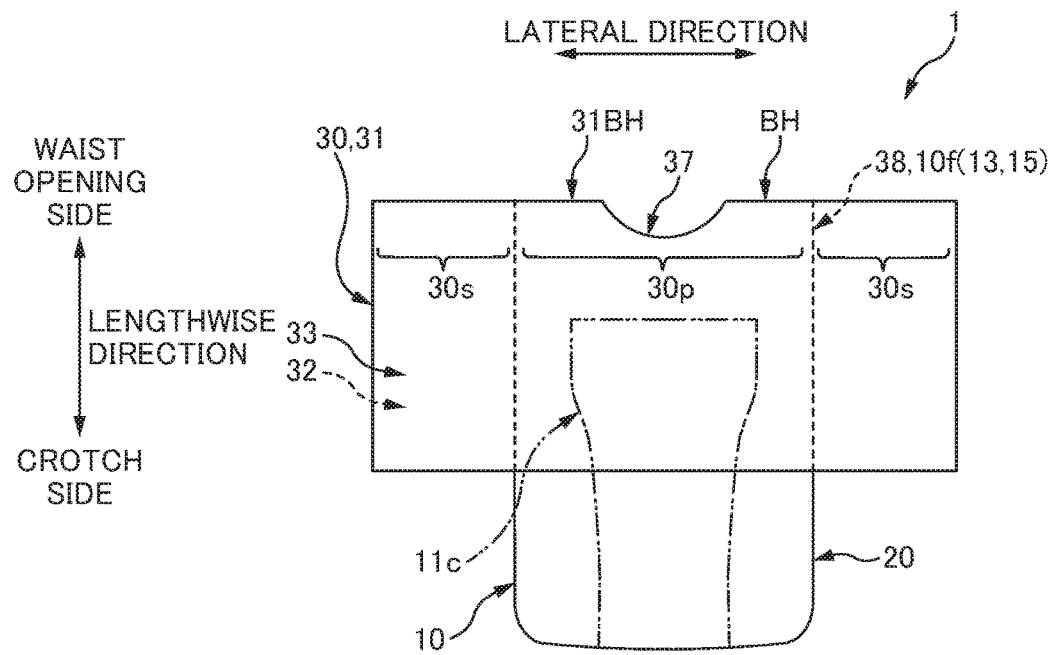
FIG. 9A and FIG. 9B are each explanatory views of modified examples of the pull-on disposable diaper 1.

FIG. 9A is an explanatory view of a modified example of the pull-on disposable diaper 1. In the aforementioned embodiment as illustrated in FIG. 6, the number of stacked sheets in the recessed portion-containing portion 30p including the recessed portion 37 in the front side portion 30 is equal to the number of stacked sheets in each of the side portions 30s, 30s located on both sides in the lateral direction of the recessed portion-containing portion 30p in the front side portion 30. In other words, both the former portion 30p and the latter portions 30s are formed by the two nonwoven fabric 32, 33 constituting the front-side band member 31, and accordingly the number of stacked sheets of each of the portions 30p, 30s are two, respectively.

On the other hand, in this modified example, a separate sheet 38 is overlapped on the recessed portion-containing portion 30p which is the former portion, and thus the number of stacked sheets in the recessed portion-containing portion 30p is greater than the number of stacked sheets in the latter side portions 30s, 30s. The modified example differs from the aforementioned embodiment mainly in this respect and is substantially equal to the aforementioned embodiment in other respects. In the following, the above difference will be mainly described.

In this modified example as illustrated in FIG. 9A, the separate sheet 38 is constituted of a sheet-like portion 10f protruding from the absorbent core 11c to the waist opening BH side in the lengthwise direction in the absorbent main body 10. In other words, the top sheet 13 and the back sheet 15 constituting the sheet-like portion 10f each extend to the waist opening BH side in the lengthwise direction and reach the recessed portion 37 of the edge portion 31BH of the waist opening BH in the front-side band member 31. The top sheet 13 and the back sheet 15 reach at least to the bottom 37b of the recessed portion 37. Consequently, the recessed portion-containing portion 30p in the front side portion 30 is constituted by four sheets increased by two sheets, i.e., the top sheet 13 and the back sheet 15, in addition to the two nonwoven fabric 32, 33 constituting the front-side band member 31. Thus, the stiffness of the recessed portion-containing portion 30p is high, thereby preventing the recessed portion 37 from being deformed in the natural state. As a result, the post-treatment tape 48 can more easily reach, through the recessed portion 37, the part 1p of the diaper which is located beyond the edge portion 31BH of the waist opening BH.

In contrast, the dimension of the absorbent main body 10 in the lateral direction is smaller than the dimension of the front-side band member 31 in the lateral direction, and thus the top sheet 13 and the back sheet 15 of the absorbent main body 10 are not disposed in the side portions 30s, 30s located on both sides in the lateral direction of the recessed portion-containing portion 30p in the front side portion 30. Accordingly, the number of stacked sheets in each side portion 30s is smaller by two than the number of stacked sheets in the aforementioned recessed portion-containing portion 30p. Consequently, the side portions 30s, 30s can be easily deformed due to their low stiffness. Thus, the diaper 1 can be made compact at the time of disposal, so that the diaper 1 is easily disposed of.

A sheet that can be used as the separate sheet 38 is not limited to the top sheet 13 and the back sheet 15 of the absorbent main body 10 described above. For example, a design sheet 38d on which some patterns such as illustrations are drawn as in FIG. 9B may be used as the aforementioned separate sheet 38. Details are as follows.

Figure 9B:
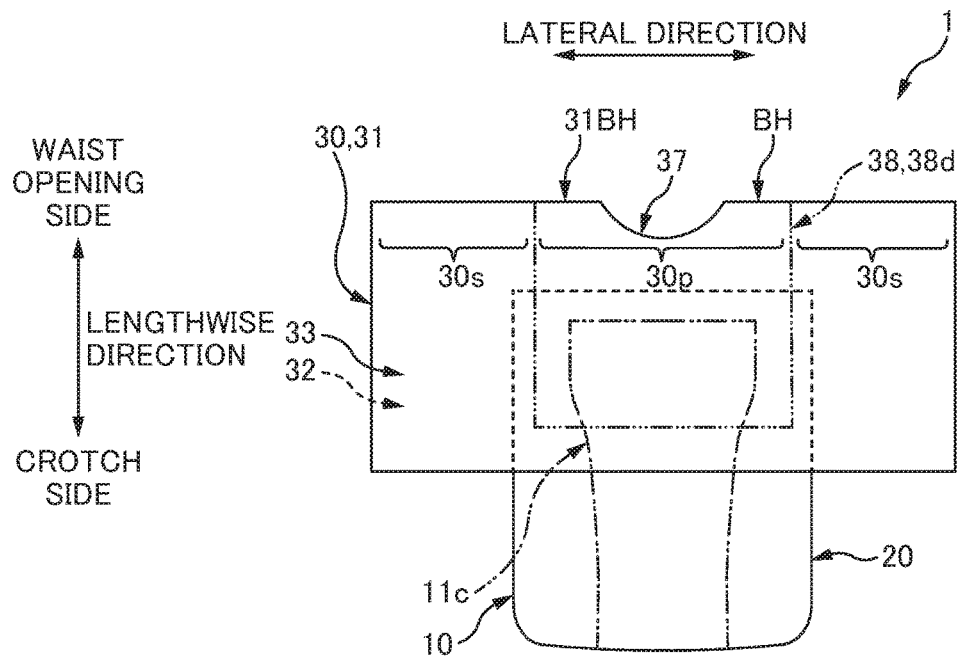

First, in this example of FIG. 9B, the design sheet 38d is overlapped on the center portion of the front-side band member 31 of the front side portion 30 in the lateral direction. Further, the design sheet 38d extends to the waist opening BH side in the lengthwise direction, thereby reaching the recessed portion 37 of the edge portion 31BH of the waist opening BH in the front-side band member 31. The design sheet 38d reaches at least the bottom 37b of the recessed portion 37. Thus, the stiffness of the recessed portion-containing portion 30p is enhanced.

In contrast, the dimension of the design sheet 38d in the lateral direction is smaller than the dimension of the front-side band member 31 in the lateral direction. Accordingly, the design sheet 38d is not disposed in the side portions 30s, 30s located on both sides in the lateral direction of the recessed portion-containing portion 30p in the front side portion 30, and thus the number of stacked sheets in each of the side portions 30s, 30s is smaller by one than the number of stacked sheets in the aforementioned recessed portion-containing portion 30p. Consequently, the stiffness of the side portion 30s, 30s can be lowered.

Other Embodiments

Although the embodiment of the present disclosure has been described as stated above, the aforementioned embodiments are for facilitating understanding of the invention, and are not limiting of the invention, and are not to be interpreted as limiting the invention. The invention can of course be altered and improved without departing from the gist thereof, and equivalents are intended to be embraced therein. For example, modifications as will be described below are possible.

In the aforementioned embodiment, an arc-shaped recessed portion 37 is exemplified as an example of the recessed portion 37 included in the edge portion 31BH of the waist opening BH of the front side portion 30. However, the invention is not limited thereto. That is, the recessed portion 37 may be a rectangular shape, a triangular shape, or a polygonal shape other than those. Further, the recessed portion 37 may be a composite shape combining curves and straight lines. Moreover, in this example, the recessed portion 37 is formed, for example, by cutting the front side portion 30; however, the recessed portion 37 may be formed by a method other than cutting. For example, when the nonwoven fabric 32, 33 are produced by depositing fiber that constitutes the front-side band member 31, fiber may be deposited so as to form the recessed portion 37.

Figure 10:
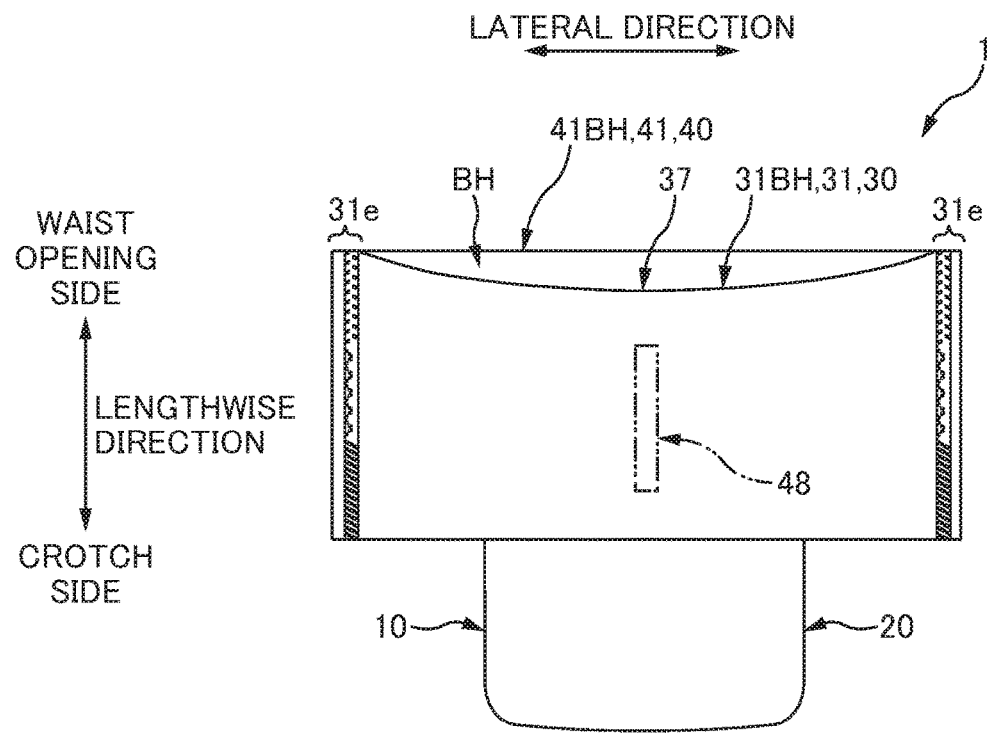
FIG. 10 is an explanatory view of another embodiment of the recessed portion 37.

In the aforementioned embodiment, as illustrated in FIG. 6, the edge portion 31BH of the waist opening BH of the front side portion 30 selectively includes the recessed portion 37 at a predetermined position in the lateral direction, such as a center position; however, the form of the recessed portion 37 is not limited thereto. For example, as in FIG. 10, the front side portion 30 may include the recessed portion 37 that is sized over the entire area of a portion in the lateral direction positioned inside from the both end portions 31e, 31e in the lateral direction. In other words, the edge portion 31BH of the waist opening BH of the front side portion 30 may include the recessed portion 37 recessed in the lengthwise direction toward the crotch portion 20 with respect to the edge portion 41BH of the waist opening BH of the back side portion 40, over the entire inner area in the lateral direction from the both end portions 31e, 31e in the lateral direction.

In the aforementioned embodiment, the three-piece type diaper 1 is exemplified as an example of the pull-on disposable diaper. However, the invention is not limited thereto. For example, the configuration of the present disclosure may be applied to a two-piece type pull-on disposable diaper including an exterior sheet that constitutes the exterior of the diaper as a first component and an absorbent main body that is fixed on the skin side surface of the exterior sheet as a second component. Also, the configuration of the present disclosure may be applied to the pull-on disposable diaper having a form in which the absorbent body is interposed between the top sheet having a substantially hourglass shape and the back sheet having a substantially hourglass shape.

Figure 11A:
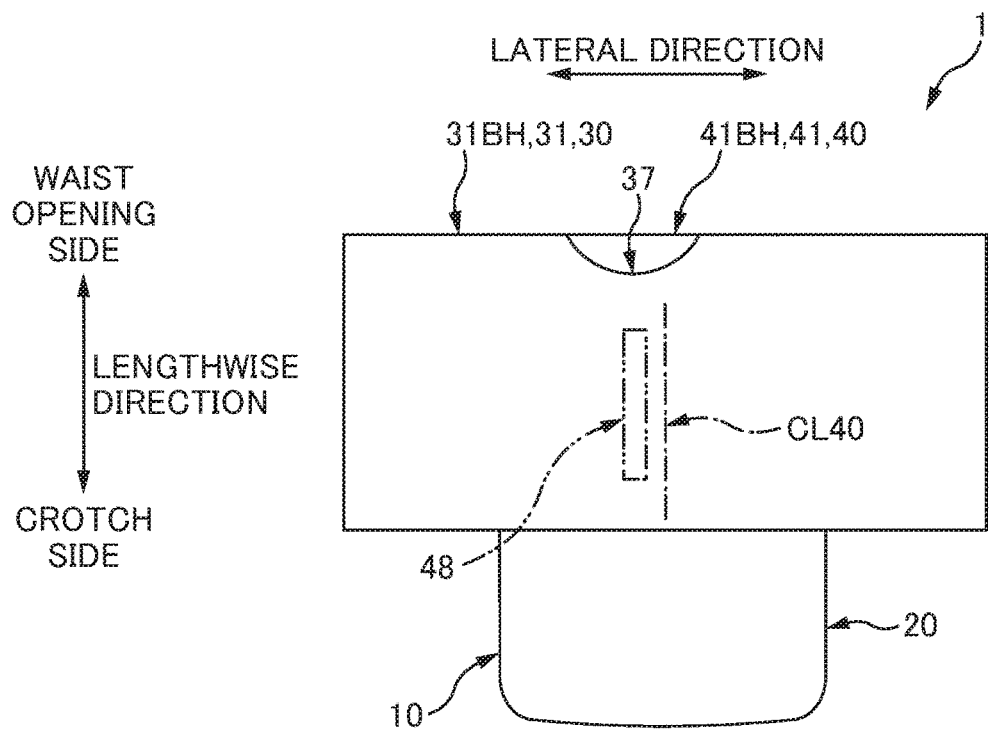
FIG. 11A and FIG. 11B are explanatory views each illustrating the position of the recessed portion 37 when each post-treatment tape 48 is located at a position other than a center part CL40 in the lateral direction.
Figure 11B:
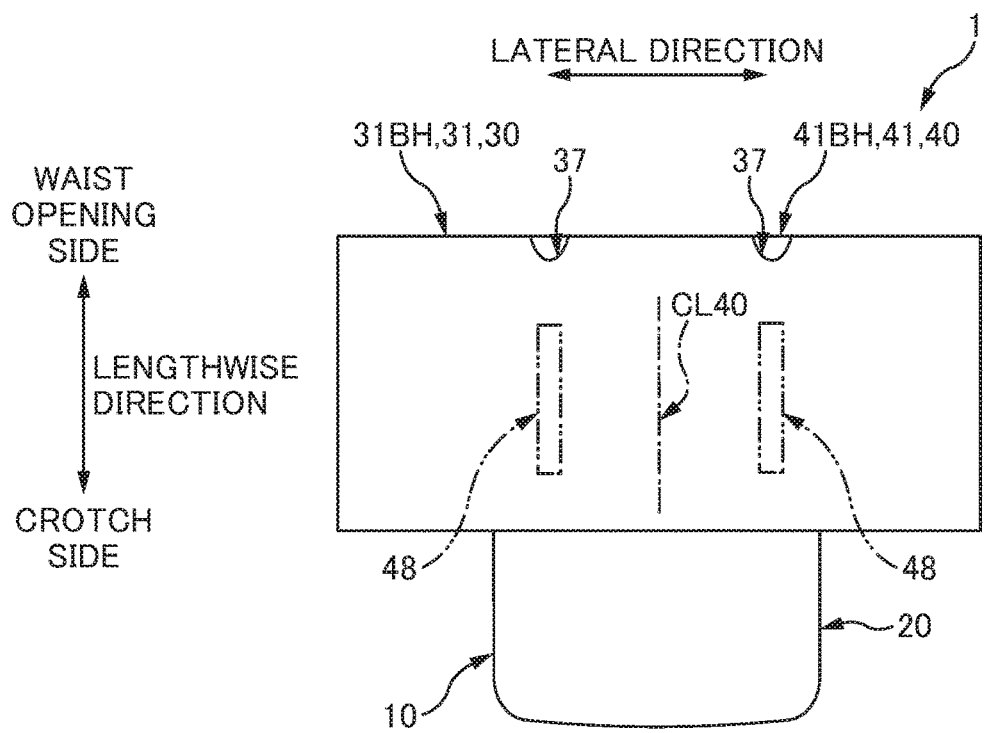

In the aforementioned embodiment, as illustrated in FIG. 6, the post-treatment tape 48 is provided at the center part CL40 of the back side portion 40 in the lateral direction, and accordingly the edge portion 31BH of the waist opening BH of the front side portion 30 includes the recessed portion 37 at the center portion in the lateral direction. However, the invention is not limited thereto. For example, as in FIG. 11A, when the post-treatment tape 48 is provided in a portion shifted in the lateral direction from the center part CL40 in the lateral direction of the back side portion 40, the edge portion 31BH of the waist opening BH of the front side portion 30 may include the recessed portion 37 at a portion shifted in the lateral direction from the center part CL40 in the lateral direction accordingly. As illustrated in FIG. 11B, when two post-treatment tapes 48, 48 are provided at parts in the lateral direction which sandwich the aforementioned center part CL40 as an example of multiple tapes, the edge portion 31BH of the waist opening BH of the front side portion 30 may include two recessed portions 37, 37 respectively at parts in the lateral direction which sandwich the aforementioned center part CL40 in the edge portion 31BH of the waist opening BH of the front side portion 30 accordingly.

The invention claimed is:

1. A pull-on disposable diaper including a lengthwise direction and a lateral direction orthogonal to each other, the pull-on disposable diaper comprising:
    a front side portion;
    a back side portion;
    a crotch portion;
    a waist opening; and
    a pair of leg openings,
    an edge portion of the waist opening of the front side portion including a recessed portion that is recessed in the lengthwise direction toward the crotch portion with respect to an edge portion of the waist opening of the back side portion,
    a tape member being fixed on a non-skin side surface of the back side portion so as to be extendable toward the waist opening in the lengthwise direction, the tape member being used for fixing the diaper in a small state in the lengthwise direction when the diaper is disposed of,
    the recessed portion being provided at a position corresponding to the tape member in the lateral direction.

2. The pull-on disposable diaper according to claim 1, wherein
    a center position of the tape member in the lateral direction is included in the recessed portion in the lateral direction.

3. The pull-on disposable diaper according to claim 1, wherein
a maximum value of a dimension of the recessed portion in the lateral direction is greater than a maximum value of a dimension of the tape member in the lateral direction.

4. The pull-on disposable diaper according to claim 1, wherein
in a state in which an edge portion of the waist opening of the back side portion and an end portion of the crotch portion in the lengthwise direction are overlapped at mutual center positions in the lateral direction by folding the diaper in two in the lengthwise direction so that the front side portion is positioned inside,
a bottom of the recessed portion does not protrude in the lengthwise direction from an edge portion of the waist opening of the back side portion.

5. The pull-on disposable diaper according to claim 1, wherein
in a state in which an edge portion of the waist opening of the back side portion and an end portion of the crotch portion in the lengthwise direction are overlapped at mutual center positions in the lateral direction by folding the diaper in two in the lengthwise direction so that the front side portion is positioned inside,
a bottom of the recessed portion protrudes from the edge portion in the lengthwise direction.

6. The pull-on disposable diaper according to claim 5, wherein
a bottom-containing portion including the bottom of the recessed portion in the front side portion includes a different color region that can be visually recognized from a skin side by a color different from a color of the end portion of the crotch portion.

7. The pull-on disposable diaper according to claim 1, wherein,
the tape member is provided at a center portion of the back side portion in the lateral direction, and
the recessed portion is formed at a center portion of the front side portion in the lateral direction.

8. The pull-on disposable diaper according to claim 7, wherein
the diaper includes an absorbent core that absorbs excrement,
the diaper includes elastic members that impart contractile force in the lengthwise direction and the lateral direction, and
in a virtual state in which the contractile force is not imparted at all,
a maximum value of a dimension of the recessed portion in the lateral direction is smaller than a maximum value of a dimension of the absorbent core in the lateral direction.

9. The pull-on disposable diaper according to claim 1, wherein
a number of stacked sheets in a recessed portion-containing portion that includes the recessed portion in the front side portion is greater than a number of stacked sheets in each of portions positioned on both sides in the lateral direction of the recessed portion-containing portion in the front side portion.

* * * * *